(12) United States Patent
Mirkin et al.

(10) Patent No.: US 7,422,696 B2
(45) Date of Patent: Sep. 9, 2008

(54) MULTICOMPONENT NANORODS

(75) Inventors: Chad A. Mirkin, Wilmette, IL (US); Lidong Qin, Evanston, IL (US); Sungho Park, Evanston, IL (US); Ling Huang, Evanston, IL (US); Sung-Wook Chung, Livermore, CA (US)

(73) Assignee: Northwestern University, Evanston, IL (US)

(*) Notice: Subject to any disclaimer, the term of this patent is extended or adjusted under 35 U.S.C. 154(b) by 506 days.

(21) Appl. No.: 11/171,894

(22) Filed: Jun. 30, 2005

(65) Prior Publication Data
US 2007/0077429 A1   Apr. 5, 2007

Related U.S. Application Data

(63) Continuation-in-part of application No. 11/062,983, filed on Feb. 22, 2005.

(60) Provisional application No. 60/661,659, filed on Mar. 14, 2005, provisional application No. 60/584,702, filed on Jun. 30, 2004, provisional application No. 60/546,641, filed on Feb. 20, 2004.

(51) Int. Cl.
*C23F 1/00* (2006.01)
*H01L 21/302* (2006.01)
*B82B 3/00* (2006.01)

(52) U.S. Cl. .............. 216/2; 216/13; 216/17; 216/19; 216/56; 216/83; 216/95; 216/96; 216/100; 216/108; 438/99; 438/694; 438/745; 438/754; 427/569; 427/243; 427/444; 427/117; 205/118; 205/149; 205/150; 205/170; 205/181; 205/220; 205/223; 977/762; 977/810; 977/849; 977/856; 977/857

(58) Field of Classification Search ............ None
See application file for complete search history.

(56) References Cited

U.S. PATENT DOCUMENTS

| 6,831,017 | B1* | 12/2004 | Li et al. ............... 438/694 |
| 7,018,549 | B2* | 3/2006 | Metz et al. ............... 216/2 |
| 7,105,052 | B1* | 9/2006 | Schlenoff ............... 117/68 |
| 7,202,173 | B2* | 4/2007 | Hantschel et al. ....... 438/694 |
| 7,225,082 | B1* | 5/2007 | Natan et al. ............... 702/27 |

(Continued)

FOREIGN PATENT DOCUMENTS

WO     WO 03/095973     11/2003

(Continued)

OTHER PUBLICATIONS

Liu et al "Nanowire Lithography: Fabricating Controllable Electrode Gaps Using Au-Ag-Au Nanowires" Nano Letters, 5 (6) 1071-1076, May 17, 2005.*

(Continued)

*Primary Examiner*—Anita K Alanko
(74) *Attorney, Agent, or Firm*—Marshall, Gerstein & Borun LLP

(57) ABSTRACT

Multicomponent nanorods having segments with differing electronic and/or chemical properties are disclosed. The nanorods can be tailored with high precision to create controlled gaps within the nanorods or to produce diodes or resistors, based upon the identities of the components-making up the segments of the nanorods. Macrostructural composites of these nanorods also are disclosed.

8 Claims, 12 Drawing Sheets

U.S. PATENT DOCUMENTS

| | | | |
|---|---|---|---|
| 2002/0104762 A1* | 8/2002 | Stonas et al. | 205/118 |
| 2003/0209427 A1 | 11/2003 | Natan et al. | |
| 2003/0211488 A1 | 11/2003 | Mirkin et al. | |
| 2004/0209376 A1* | 10/2004 | Natan et al. | 436/56 |
| 2006/0054506 A1* | 3/2006 | Natan et al. | 205/112 |
| 2006/0292839 A1* | 12/2006 | Yi et al. | 438/570 |

FOREIGN PATENT DOCUMENTS

WO    WO 2007040558 A2 * 4/2007

OTHER PUBLICATIONS

Sandrock et al "Synthesis and Linear Optical Properties of Nanoscopic GOld Particle Pair Structures" J Phys Chem B, 103, 11398-11406, Dec. 3, 1999.*
Ji et al "Fabrication of nanoporous gold nanowires" Appl Phys Lett, 81 (23) 4437-4439, Dec. 2, 2002.*
Yin et al "Silver Nanowires Can Be Directly Coated with Amorphous Silica To Generate Well-Controlled Coaxial Nanocables of Silver/Silica" Nano Letters, 2 (4) 427-430, Feb. 2, 2002.*
Sioss et al "Batch Preparation of Linear Au and Ag Nanoparticle Chains via Wet Chemistry" Nano Letters, 5 (9) 1779-1783, Aug. 4, 2005.*
Qin et al "On-Wire Lithography" Science, 309, 113-115, Jul. 1, 2005.*
Keating et al "Striped Metal Nanowires as Building Blocks and Optical Tags" Adv Mater, 15 (5) 451-454, Mar. 4, 2003.*
Abthagir et al., *J Appl Polym Sci*, 81:2127 (2001).
Alberts et al., Molecular Biology of the Cell, 4th Ed., Garland Science Inc.:New York, pp. 483-484 (2002).
Bauer et al., Langmuir, 19:7043 (2003).
Birenbaum et al., Langmuir, 19:9580 (2003).
Bruchez et al., Science, 281:2013 (1998).
Bucak, et al., *Biotechnol. Prog.* 19:477 (2003).
Cao et al., Science, 297:1536 (2002).
Caswell et al., J. Am. Chem. Soc., 125:13914 (2003).
Chou et al., *Science*, 272:85 (1996).
Clemmit, et al., *Biotechnol. Bioeng.* 67:206 (2003).
Cress et al., *Promega Notes Magazine*, 42:02 (1993).
Crommie et al., Science, 262:218 (1993).
Cui et al., Science, 293:1289 (2001).
De Boer, et al., J. *Proc. Natl. Acad. Sci. U.S.A.* 100:780 (2003).
Dyr, et al., *J. Chromatogr. B* 699:383 (1997).
Erhardt et al., Chem Mater, 12:3306 (2000).
Fexby, *Trends Biotechnol.*, 22:511 (2004).
Gates et al., Chem Rev, 105:1171 (2005).
Ginger et al., Angew Chem Int Ed, 43:30 (2004).
Godat, et al., *MagneHis™ protein purification system technical manual*, (Promega, corp., WI, USA) (2003).
Graham et al, *Virol.*, 52:456 (1973).
Gu et al., J. Am. Chem. Soc., 125:15702 (2003).
Gudiksen et al., *Nature*, 415:617 (2002).
Heath et al., Chem Phys Lett, 208:263 (1993).
Hua et al., *Nano Lett*, 4:2467 (2004).
Hultgren et al., J. Appl. Phys., 93:7554 (2003).
Keating et al., Adv. Mater., 15:451 (2003).
Khng et al., *Biotechnol. Bioeng.* , 60:419 (1998).
Kuhara, et al., *Anal. Chem.*, 76:6207 (2004).
Ieong et al., *Science*, 306:2057 (2004).
Iijima et al., *Nature*, 363:603 (1993).
Kniepp et al., *Chem Rev*, 99:2957 (1999).
Kovrtyukhova et al., *J Phys Chem B*, 105:8762 (2001).
Kovrtyukhova et al., *Chem Eur J*, 8:4354 (2002).
Lee et al., Science, 295:1702 (2002).
Lee et al., *Angew Chem Int Ed*, 43:3048 (2004).
Li et al., *App Phys Lett*, 77:3995 (2000).
Linder, et al., M. E. *Biochemistry*, 43:11873 (2004).
Liu et al., *Nano Lett*, 4:671 (2004).
Lopez et al., J. Am. Chem. Soc., 115:10774 (1993).
Maier et al., *Nature Mater*, 2:229 (2003).
Maier et al., *Phys Rev B*, 65:193408 (2002).
Martin, *Acc Chem Res*, 28:61 (1995).
Martin, *Science*, 266:1961 (1994).
Mascagni, P.; Ball, H. L.; Bertolini, G. *Analytica Chimica Acta*, 352:375 (1997).
Melosh et al., *Science*, 300:112 (2003).
Meyer, D. E. *Nat. Biotechnol.* 17:1112 (1999).
Mitchell, et al., *J. Am. Chem. Soc.*, 124:11864 (2002).
Morag, et al., *Anal. Biochem.* 243:257 (1996).
Morag, et al., *Biochem. J.* 316:193 (1996).
Morales et al., *Science*, 279:208 (1998).
Nam et al., *Angew. Chem. Int. Ed.*, 43:1246 (2004).
Nicewarner-Pena et al., *Science*, 294:137 (2001).
Niemeyer, et al., *Angew. Chem. Int. Ed.*, 40:3685 (2001).
Noubhani, et al., X. *J. Chromatogr. B*, 790:153 (2003).
Ong, et al., *Trends Biotechnol*, 7:239 (1989).
Park et al., Science, 295:1503 (2002).
Park et al., *App Phys Lett*, 75:301 (1999).
Park et al., *Science*, 303:348 (2004).
Peng, et al., C. *J. Biotechnol.*, 111:51 (2004).
Penn et al., *Curr. Opin. Chem. Biol.*, 7:609 (2003).
Pena et al., *J. Phys Chem B*, 106:7458 (2002).
Pet system manual, (Novagen, Inc., WI, USA) (2003).
Piner et al., *Science*, 283:661 (1999).
Rechberger et al., *Optics Comm*, 220:137 (2003).
Reed et al., *Science*, 278:252 (1997).
Reichert et al., *Phys. Rev. Lett.*, 88:176804 (2002).
Reiss et al, *Electroanal. Chem.*, 522:95 (2002).
Rigaut, et al., *Nat. Biotechnol.* 17:1030 (1999).
Routkevitch et al., *Chem Phys*, 210:343 (1996).
Routkevitch et al., *J. Phys Chem*, 100:14037 (1996).
Salem et al., *Nat. Mater.*, 2:668 (2003).
Schuck et al., *Phys Rev Lett*, 94:017402 (2005).
Smith, et al., *Nucleic Acids Res.*, 26:1414 (1998).
Son, et al., *J. Am. Chem. Soc.* 127:7316 (2005).
Stiborova, et al., *Biotechnol. Bioeng.* 82:605 (2003).
Stolz, et al., *FEBS Lett.* 377:167 (1995).
Storhoff et al., J. Am. Chem. Soc., 120:1959 (1998).
Stoscheck, et al., *Methods in Enzymology* 182:50 (1990).
Taton, et al., *Science* 289:1757 (2000).
Tatsumi, et al., *Anal. Biochem.*, 243:176 (1996).
Thess et al., *Science*, 273:483 (1996).
Tucker, Grisshammer, R. *Biochem. J.* 317:891 (1996).
Van Reis et al. *Curr. Opin. Biotechnol.*, 12:208 (2001).
Watanabe et al., *Macromolecules*, 26:4231 (1989).
Xia et al., *Chem Rev*, 99:1823 (1999).
Xiang et al., *Angew Chem Int Ed*, 44:1265 (2005).
Zhao, et al., *Am. Chem. Soc.*, 125:11474 (2003).
Zhu et al., Science, 293:2101 (2001).

* cited by examiner

MULTICOMPONENT NANORODS

CROSS-REFERENCE TO RELATED APPLICATIONS

This application is a continuation-in-part of U.S. patent application Ser. No. 11/062,983, filed on Feb. 22, 2005, which claims the benefit of U.S. Provisional Application Ser. No. 60/546,641, filed Feb. 20, 2004. This application also claims the benefit of U.S. Provisional Application Ser. No. 60/584,702, filed Jun. 30, 2004, and U.S. Provisional Application Ser. No. 60/661,659, filed Mar. 14, 2005.

STATEMENT OF GOVERNMENTAL INTERESTS

This invention was made with government support under Air Force Office of Scientific Research (AFOSR) grants F49620-00-1-0283 and F49620-02-1-0180, National Science Foundation grant EEC-0118025, and Defense Advanced Research Projects Agency (DARPA) grant DAAD-19-03-1-0065 and DARPA Spintronics grant MDA972-03-1-0023. The government has certain rights in this invention.

FIELD OF THE INVENTION

The present invention relates to nanoscale compositions for use as nanoresistors and nanodiodes, and to nanoscale compositions and methods of forming nanogap wires and nanodisk/rod arrays. In particular, the present invention relates to hybrid organic/inorganic nanocompositions to form diodes and resistors, and to inorganic compositions and on-wire lithographic methods of forming nanoelectrodes, as well as nanodisk and nanorod arrays.

BACKGROUND OF THE INVENTION

There are two general challenges in nanoscience and nanotechnology. One challenge is to fabricate nanoarchitechtures, such as nano-electrodes, diodes, and resistors, in less than 10 nanometer (nm) resolution. The second challenge is to assemble nanostructures into patterns, such as nanorod or nanodisk arrays, in a regular arrangement, with precise control and high throughput (Gates et al., *Chem Rev*, 105, 1171, 2005; Ieong, et al., *Science*, 306, 2057, 2004).

Several routes for synthesizing nanostructures have been developed. Many of these new structures have interesting electronic, optical, and chemical sensor properties that derive from their size, composition, and shape (Iijima et al., *Nature*, 363, 603, 1993; Thess et al., *Science*, 273, 483, 1996; Heath et al, *Chem Phys Lett*, 208, 263, 1993; Morales et al, *Science*, 279, 208, 1998; Martin, Science, 266, 1961, 1994; Martin, *Acc Chem Res*, 28, 61, 1995; Routkevitch et al, *Chem Phys*, 210, 343, 1996). However, methods of synthesizing multicomponent materials made from both organic and inorganic materials are few (Gudiksen et al, *Nature*, 415, 617, 2002; Lee et al, *Angew Chem Int Ed*, 43, 3048, 2004; Kovtyukhova et al, *J Phys Chem B*, 105, 8762, 2001; Pena et al, *J Phys Chem B*, 106, 7458, 2002; Park et al, *Science*, 303, 348, 2004; Nicewarner-Pena et al; *Science*, 294, 137, 2001).

Porous templates offer an ability to routinely generate such multicomponent materials through two distinct methods. Both rely on the use of electrochemistry to generate an initial segment of metal from a plating solution. However, one method utilizes layer-by-layer chemisorption processes (Kovtyukhova et al, *J Phys Chem B*, 105, 8762, 2001), to build organic segments on top of a preformed metal segment, while the second method utilizes conducting polymer monomers combined with an appropriately applied potential to polymerize the monomer within the template at the metal segment solution interface (Park et al, *Science*, 303, 348, 2004). An advantage of the latter approach is that it provides excellent control over the segment length of the metal and organic regions of the structure, simply by controlling the number of Coulombs (C) that are passed in the experiment. This disclosure provides another approach, based upon this synthetic strategy, for preparing hybrid multicomponent (e.g., organic-inorganic or metal-metal) nanorods having electronic properties derived from their compositions, wherein the spatial distribution of the different compositional segments can be precisely controlled.

Lithography is a powerful way of processing substrates for use in many practical applications, including semiconductor and optical industries. Many methods of printing structures on flat substrates are known, and some methods for printing on large curved architectures are also known (Melosh et al, *Science*, 300, 112, 2003; Chou et al, *Science*, 272, 85, 1996; Xia et al, *Chem. Rev.*, 99, 1823, 1999; Erhardt et al, *Chem. Mater.*, 12, 3306, 2000).

Fabricating features on any of these substrates at the micron to macroscopic length scale is now routine, and with advances in nanotechnology, it is possible to print a limited set of structures made from a variety of hard and soft materials with size control of features down to ten nanometers (Crommie et al, *Science*, 262, 218, 1993 and Hua et al, *Nano Lett.*, 4, 2467, 2004). Although they have many attributes and capabilities, nanolithographic techniques, such as electron beam lithography, dip-pen nanolithography (DPN), focused ion-beam lithography, and nanoimprint lithography, are limited with respect to throughput, materials compatibility, resolution, and/or cost (Gates et al, *Chem. Rev.*, 105, 1171, 2005). For example, the field of nanoelectronics relies upon the ability to fabricate and functionalize less than 20 nm, i.e., sub-20 nm, electrode gaps for precise electrical measurements on nanomaterials. Fabricating such structures is far from routine and often involves low-yielding, imprecise, and difficult-to-control procedures, such as break junction techniques and gap narrowing by electroplating (Reed et al, *Science*, 278, 252, 1997; Park et al, *App Phys Lett*, 75, 301, 1999; Li et al, *App Phys Lett*, 77, 3995, 2000; Xiang et al, *Angew Chem Int Ed*, 44, 1265, 2005). Other methods of preparing nanorods having different segments are disclosed in U.S. Patent Application Publication Nos. 2003/0209427, 2002/0104762 and 2004/0209376.

The present invention is directed to resistors and diodes composed of nanorods produced in a high-throughput procedure that allows for the systematic creation of large quantities of identical nanorods in an aligned array. These nanorods are then facilely used as diodes or resistors; depending upon the components of the nanorod and their electronic properties. The present invention provides a method of generating assembled nanorod structures with control over both the length of, the distance, between, and the electronic properties of rods, allowing for the formation of novel resistors and diodes.

The present invention is also directed to a new, general, and relatively high throughput procedure for lithographically processing one-dimensional arrays of nanodisks in which the sizes of the gaps between disks can be controlled down to the 5 nm length scale. This procedure, termed on-wire lithography (OWL), combines advances in template directed synthesis of nanowires with electrochemical deposition and wet-chemical etching, and allows the routine fabrication of architectures previously considered difficult, if not impossible, to manufacture via any known lithographic methodology. The present invention provides a method, through OWL, of generating one-dimensionally assembled nanorod structures and nanodisk arrays, with control over both the length of, and the distance between, rods or disks respectively.

SUMMARY

The present invention relates to nanostructures having electronic properties that can be assembled in a regular and repeatable manner.

Therefore, one aspect of the present invention is to provide multicomponent nanorods comprising discrete polymeric and metallic segments, optionally further modified with segments comprising a semiconductor or a metal with a low work function.

Another aspect of the invention is to provide nanostructures having the electronic properties of diodes or resistors.

Yet another aspect of the invention is to provide of method of manufacturuing multicomponent nanorods in a controlled manner, such that the nanorods can be produced with tailorable segments of metal, polymer, and optionally, semiconductors or metals with low work function.

Still another aspect of the invention is to provide aggregates of multicomponent nanorods wherein the nanorod comprises both hydrophobic and hydrophilic regions, and wherein the characteristics and spatial distributions of the hydrophobic and hydrophilic regions determine and control the structure of the aggregate.

Yet another aspect of the invention is to provide a lithographic method of producing nanowires comprising impervious metals and having gaps at positions previously containing a sacrificial metal, wherein the lithographic method is compatible with a high-through-put production and with a high level of precision.

A further aspect of the invention is to provide nanowires and nanoarrays produced from the lithographic process for use in microelectrode circuitry.

DETAILED DESCRIPTION OF THE PREFERRED EMBODIMENTS

The present invention is directed to nanostructures having electronic properties or applications. More particularly, the present invention is directed (a) to organic/inorganic hybrid nanostructures for use as diodes or resistors and (b) to multi-component nanowires and nanoarrays synthesized with high accuracy and an exquisite control of gaps. Assembled macrostructures of these nanowires also are disclosed.

Figure 4:
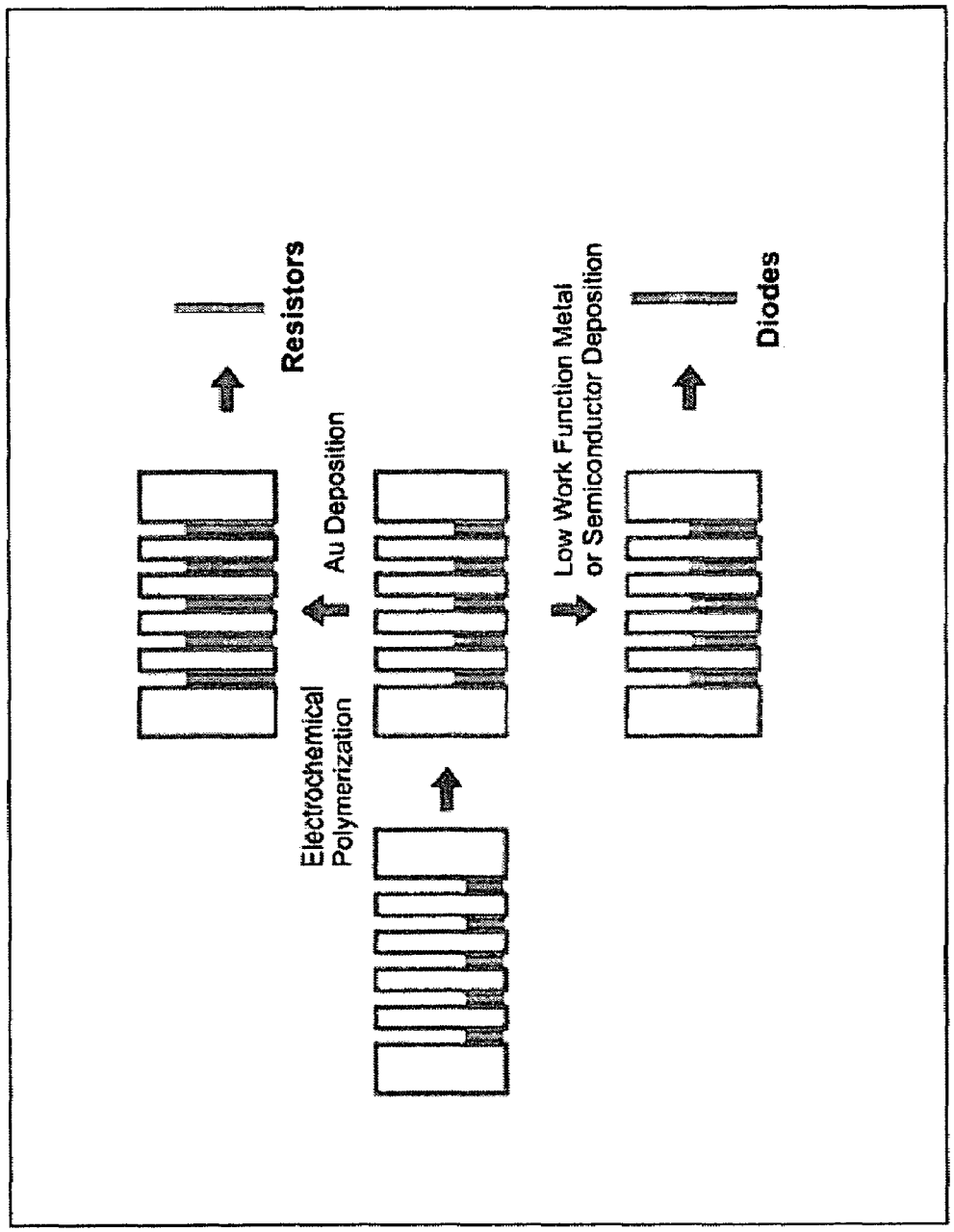
FIG. 4 is a schematic of the method of synthesizing multicomponent inorganic-organic hybrid nanorod structures.
Figure 5:
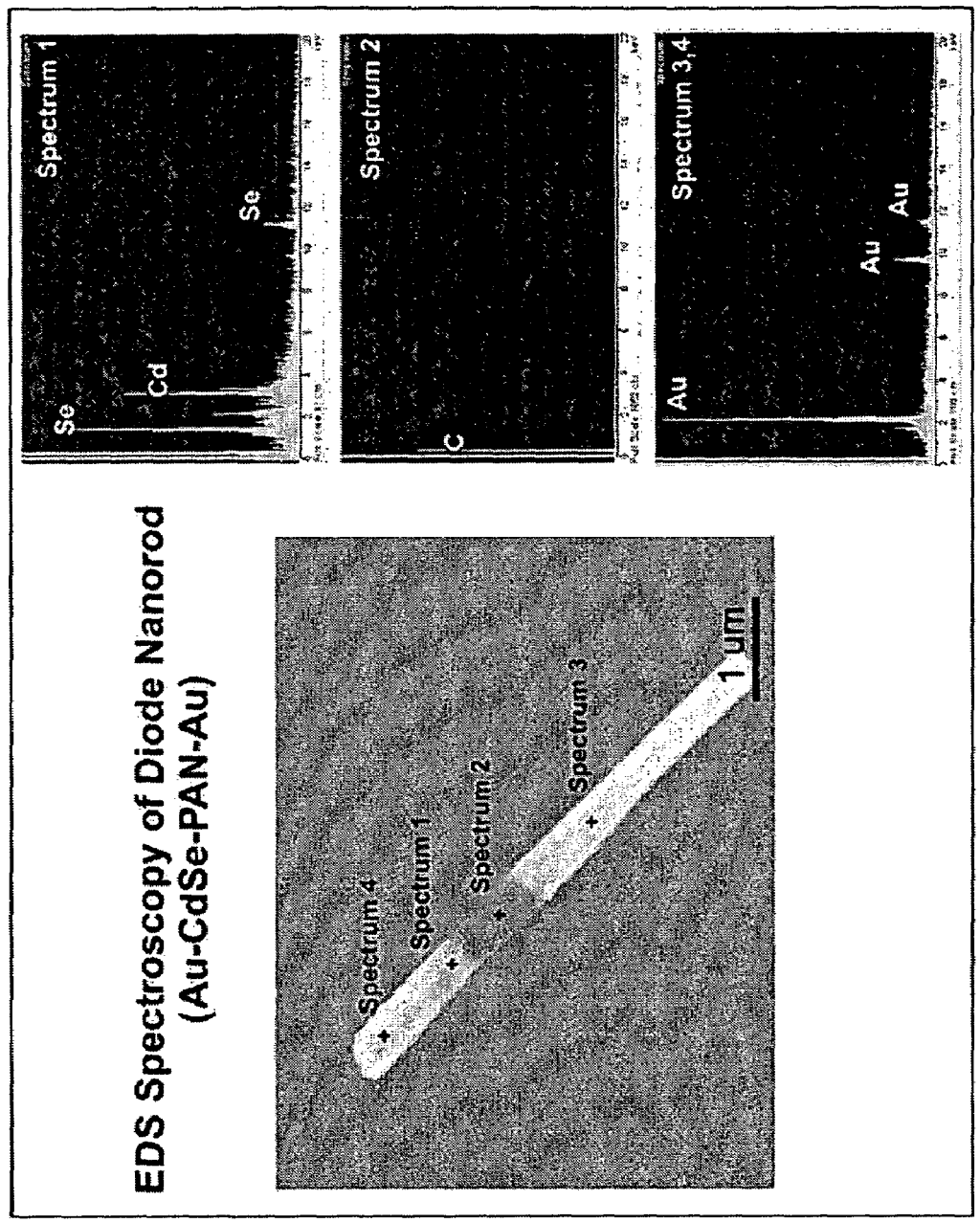
FIG. 5 is the FESEM image and corresponding EDX images for each segment of a single four-segmented gold-cadmium selenide-polyaniline-gold (Au—CdSe—PAN-Au) nanorod.

Multicomponent rod-like structures containing segments of metals and polymers can be systematically synthesized via template-assisted in-situ electrochemical deposition, such that the rod structures can be tailored through a choice of individual segment compositions that exhibit desired electrical behavior in the context of an integrated microelectrode device. The length of the each segment can be controlled by monitoring the charge passed during the electro-deposition process. FIG. 4 is a schematic illustrating the present method of producing hybrid organic/inorganic (e.g., polymer/metal) nanorod structures. Nanorods comprising metal and polymer segments optionally can be combined with a segment of an inorganic semiconductor or a metal with a low work function. These optional segments further modify the electronics of the nanorod to provide a wide range of practical applications.

In the method of preparing hybrid organic-inorganic nanorods, segmented metal-polymer nanorods are synthesized by electrochemical deposition of a metal, e.g., Au, onto an alumina template, followed by electrochemical polymerization of the organic monomer (e.g., pyrrole). A second electrochemical deposition of Au provides a resistor. An electrochemical deposition of a semiconductor or low work function metal provides a diode. See FIG. 4. The length of each metal and polymer segment is controlled by monitoring the charge passed during the electrochemical deposition process.

As used herein, "nanostructure" and "nanorod," refer to small structures that are less than 10 μm, and preferably less than 5 μm, in any one dimension and that have a length to width ratio greater than one As used herein, "nanoarray" refers to groups of uniformly spaced nanostructures.

As used herein, "multicomponent" refers to an entity that comprises more than one type of material. For example, a multicomponent nanorod refers to a nanorod having sections of different materials, e.g., a nanorod with an Au segment and a Ppy segment or a nanorod with an Au segment and a Ni segment.

As used herein, "polymer" means any material of repeating units suitable for deposition using electrochemistry. In some embodiments, the polymer is a polypyrrole. In other embodiments, the polymer is a polyaniline. Examples of other polymers include, but are not limited to, polythiophene, poly (ethylenedioxy)thiophene, compounds of poly(heteraromic vinylenes), polyvinylphosphate, and mixtures thereof. The monomers comprising the above-listed polymers can be components of copolymers as well. Optionally, the polymer can comprise an acceptable salt, e.g., tetrafluoroborate, and/or be doped with another polymer, e.g., poly(styrene p-sulfate). The polymer can be modified with optional substituents on an aryl ring of the corresponding monomer. Nonlimiting examples of such aryl substituents include, but are not limited to, cyano, sulfate, and nitro. Other suitable counterions, polymers for doping, or optional aryl ring substituents are well known to those of skill in the art.

The metal component of the nanorod can be any metal compatible with in-situ electrochemical deposition. Examples of such metals include, but are not limited to, indium-tin-oxide, titanium, platinum, titanium tungstide, gold, silver, nickel, copper, and mixtures thereof.

The optional inorganic semiconductor can be any material displaying semiconducting properties. Examples of inorganic semiconductors for use in the present disclosure include, but are not limited to, cadmium selenide, zinc selenide, cadmium telluride, zinc telluride, cadmium-tellurium selenide, copper-indium selenide, copper oxide, copper sulfide, silicon, germanium, compounds and alloys of silicon and germanium, gallium arsenide, gallium phosphide, gallium nitride, cadmium sulfide, zinc sulfide, titanium oxide, zinc oxide, tungsten oxide, molybdenum oxide, titanium sulfide, or mixtures thereof.

As used herein, a metal with low work function is a metal, such as, but not limited to, aluminum, magnesium, calcium, silver, or cadmium.

Nanoarrays formed from multicomponent nanorods can be used as multiple individually addressable microelectrodes. Multiple individually addressable microelectrodes allow one to electronically address the nanostructure at different points along its long axis.

Figure 2:
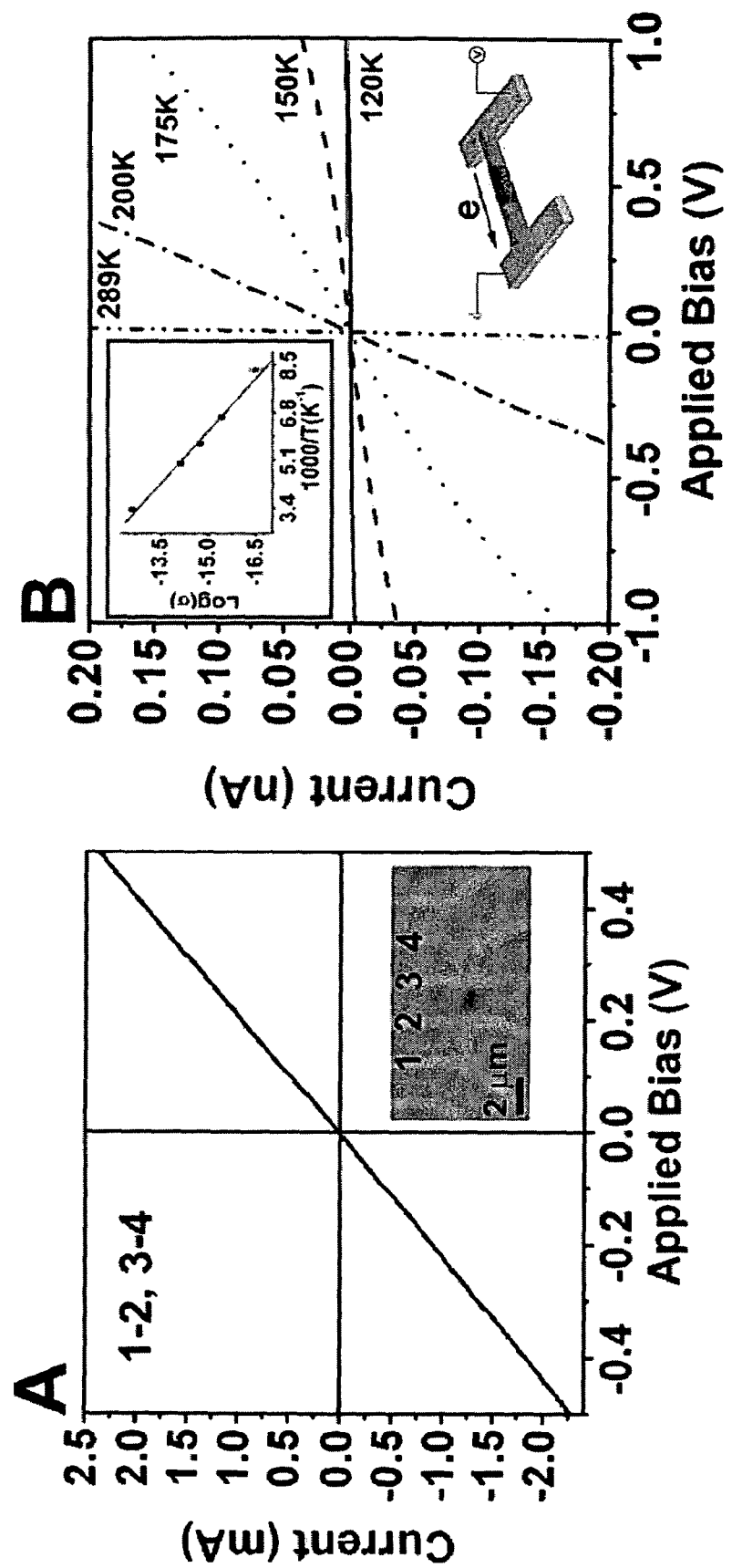
FIG. 2A is a current-voltage (I-V) measurement for Au segments within a single nanorod, at room temperature, with an inset showing the optical microscope image of a single Au-Ppy-Au nanorod on prefabricated microelectrodes
FIG. 2B shows temperature dependent I-V curves for measurements across electrodes 2 and 3 with an inset showing a plot of log σ(T) vs 1/T, wherein σ is conductivity.

Multicomponent nanorods can be used as electronic components as determined by the compositions of their segments. For example, the Au portions of the nanorod exhibit linear I-V characteristics and bulk metallic behavior at room temperature. Linear I-V plots over a voltage range of −1 to +1 volts (V) demonstrate Ohmic behavior. Such segments can be used as electrical contacts and conductors. Significantly, I-V measurements across the Ppy segment of the Au-Ppy-Au nanorod (FIG. 2B) also exhibit a linear response at room temperature, but non-linear behavior at low temperatures (<175 K), characteristic of a semiconductor (see FIG. 2B). Such segments and arrangements of segments can be used as active electronic components such as diodes. Therefore, the multicomponent nanorods are contemplated for use as nano-scale semiconductors and/or electronic components of microelectrodes.

Figure 1:
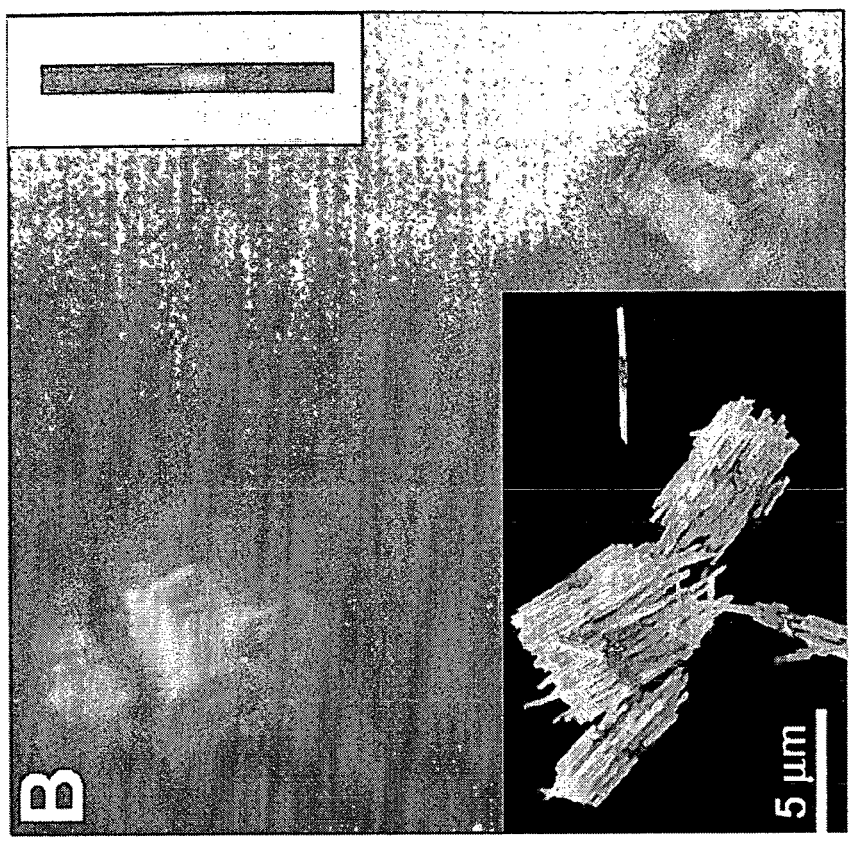
FIG. 1A is an optical microscope image of gold-polypyrrole-gold (Au-Ppy-Au) nanorods.
FIG. 1B is an optical microscope image of gold-polypyrrole-cadmium-gold (Au-Ppy-Cd—Au) nanorods with an inset of a corresponding field emission electron scanning microscopy (FESEM) image.
Figure 1:

Four segment nanorods (e.g., Au-Ppy-Cd—Au) can be prepared via analogous procedures. The optical microscopy and field emission electron scanning microscopy (FESEM) images of such rods exhibit clear contrast between the three different chemical compositions (bright Au ends, dark Ppy, and white Cd, see FIG. 1B). Other nanorods containing more segments also are contemplated. In particular, nanorods having five, six, seven, eight, and even higher numbers of segments can be prepared using the method disclosed herein. The end use of the resulting nanorod will dictate the number of segments, the order of the segments, and the composition of each segment. Each of these parameters easily can be determined by a person of skill in the art, in combination with the disclosure herein.

In accordance with the present invention, one can systematically synthesize multicomponent nanorods that contain metals, inorganic semiconductors, and polymers via template-assisted in-situ electrochemical depositions, and that such rod-structures can be tailored through choice of segment composition to exhibit resistor or diode like behavior in the context of an integrated microelectrode device. The approach can be contrasted with the alternative layer-by-layer approach for synthesizing multicomponent rod structures in two ways. First, the electrochemical approach offers greater control over the architectural parameters of the resulting structures (in particular segment length). Second, the properties (e.g., turn on voltages) of the resulting structures substantially differ, even when comparable materials are used. It is theorized that this difference is attributed to junctions formed in the layer-by-layer approach being less well defined because the active materials are introduced as a polymer particle dispersion with little control over where the active interface is formed. In the present electrochemical approach, only conducting materials can be deposited within the pores. The present invention is a powerful method for producing nanostructures having predetermined desirable electrical properties by a straightforward synthetic procedure that offers a high degree of reproducibility. The nanostructures can be used in a wide range of electronic and sensor devices (Liu et al, *Nano Lett*, 4, 671, 2004).

Multicomponent nanorods produced from template-assisted in-situ electrochemical depositions can be tailored such that components of like polarity (hydrophobicity or hydrophilicity) are deposited on one end of the nanorod while components of opposite polarity are deposited on the other end of the nanorod. Such multicomponent nanorods are suitable for assembly into aggregate structures in a manner similar to the formation of liposomes or micelles.

As used herein, "polarity" is an assessment of a component's hydrophobic or hydrophilic character. Components aggregate or associate with components of like polarity, i.e., polar components with other polar components, and non-polar components with non-polar components.

Aggregation of nanorods having both polar and non-polar components grouped at opposite ends of the nanorod will occur via the alignment of the polar components and alignment of the non-polar components. This aggregation will result in a "fanning" or micelle-like arrangement of multi-component nanorods into nano-disks, spheres, cylinders and other structures.

Another embodiment of the present process of segment-by-segment formation of nanostructures is the formation of nanogap wires and nanodisk and nanorod arrays. These wires, disks, and arrays have electronic properties that can be tailored from their compositional components (i.e., the identities of the metals forming the nanocompositions). The use of metals having different chemical and electrical properties allows the creation of gaps in these nanowires where the nanowire is treated with a solution that dissolves a certain metal but not the other metal. These nanogaps allow the formation of facing electrodes with controlled gaps, which is an important goal of nanoelectronics. In particular, this method allows for the facile and controlled formation of arrays of such facing electrodes. This technique of selectively stripping out, or etching, one metal segment type (i.e., the sacrificial metal segment) in the presence of different metal segment types to form gaps has been named on-wire lithography (OWL).

As used herein, the term "nanowire" refers to the product of on-wire lithography, comprising coated nanorods that have been subjected to etching to dissolve a sacrificial metal, leaving gaps where the sacrificial metal segments were positioned prior to etching.

As used herein, the term "sacrificial metal" refers to a metal that can be dissolved under the proper chemical conditions. Examples of sacrificial metals include, but are not limited to, nickel which is dissolved by nitric acid, and silver which is dissolved by a methanol/ammonia/hydrogen peroxide mixture.

As used herein, the term "etching" refers to a process of dissolving a sacrificial metal segment using conditions suitable for dissolving or removing the metal comprising the sacrificial segment. As mentioned above, such etching solutions include, but are not limited to, nitric acid and a methanol/ammonia/hydrogen peroxide mixture.

As used herein, "coating" refers to a material that is positioned to contact one side of a multicomponent nanorod. The purpose of the coating is to provide a bridging substrate to hold segments of the etched nanorod together after removal of the intervening sacrificial metal segments in the etching process. Nonlimiting examples of coatings used in this invention include a gold/titanium alloy and silica.

Figure 6:
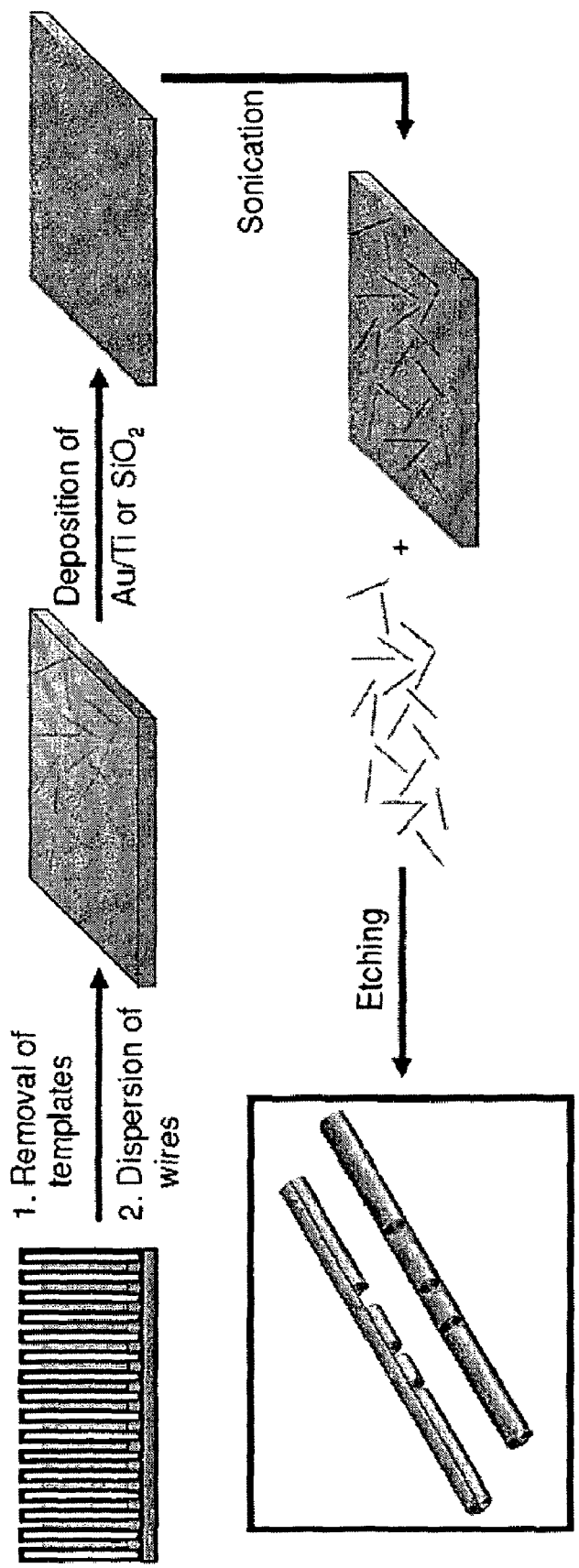
FIG. 6 is a schematic of the on-wire lithography (OWL) process.

A method of preparing nanogap wires of the present disclosure is summarized in FIG. 6. OWL is based upon manufacturing segmented nanowires comprising at least two materials, one that is susceptible to, and one that is resistant to, wet chemical etching. There are a variety of material pairs that can be used. Au—Ag and Au—Ni are two such examples of metal pairs of differing chemical properties. The sacrificial metal in these pairs are Ag and Ni, respectively. However, any combination of metals having contrasting susceptibility to chemical etching conditions can be used.

Figure 10:
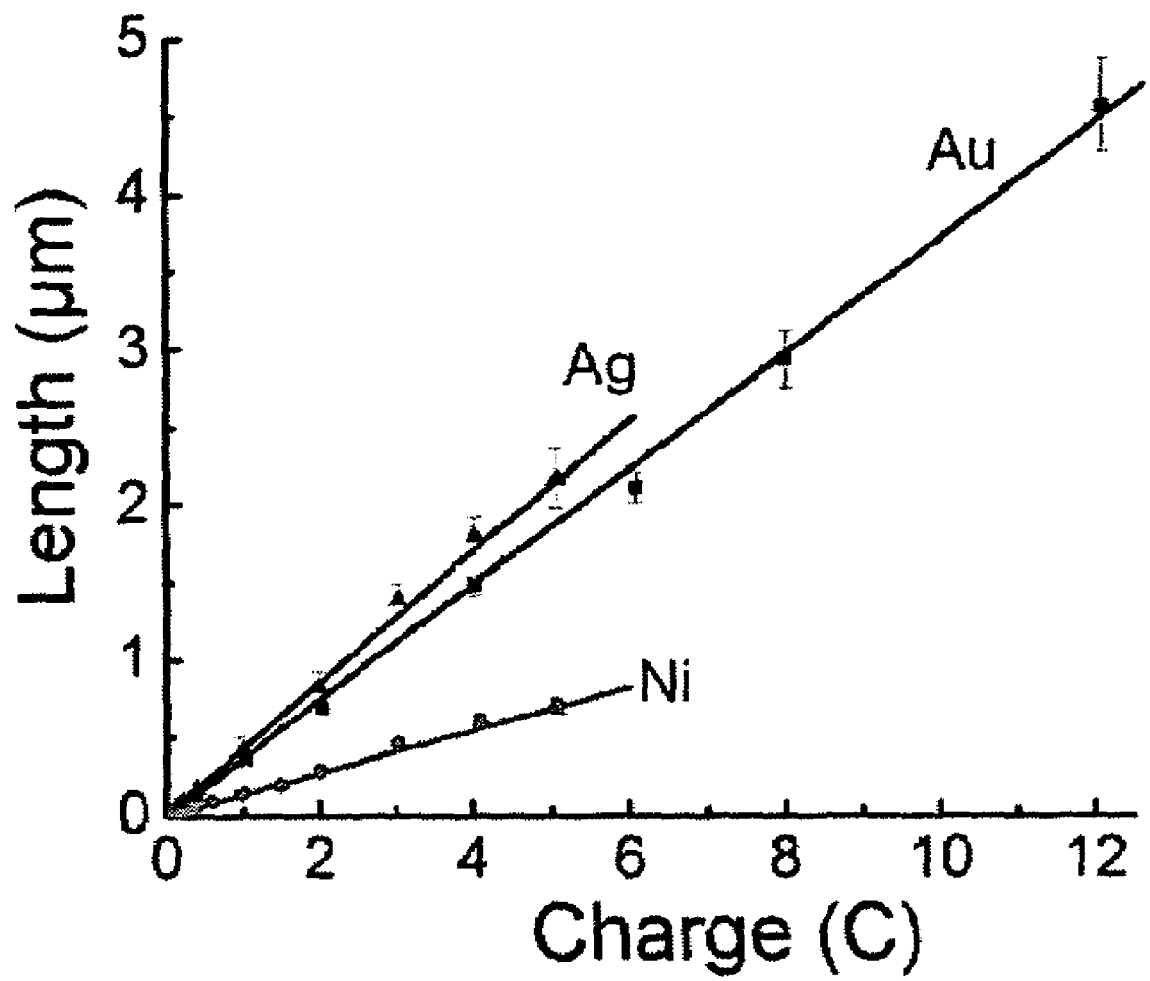
FIG. 10 is a graph of length vs. charge passed during electrochemical deposition of Ag, Au, and Ni.

Using the OWL procedure, nanowires having desired gaps of 5, 25, 40, 50, 70, 100, 140, and 210 nm, for example, can be prepared (FIG. 7A-7F). Other desired gap sizes of about 5 nm to about 250 nm can be prepared. The gap size of the nanowire is directly correlated to the segment size of the sacrificial metal segment. Sacrificial metal segment size is controlled by monitoring the current passed during its deposition (FIG. 10). A nanowire can have sacrificial metal segments of different size, as determined by the desired end use of the nanowire.

Figure 8:
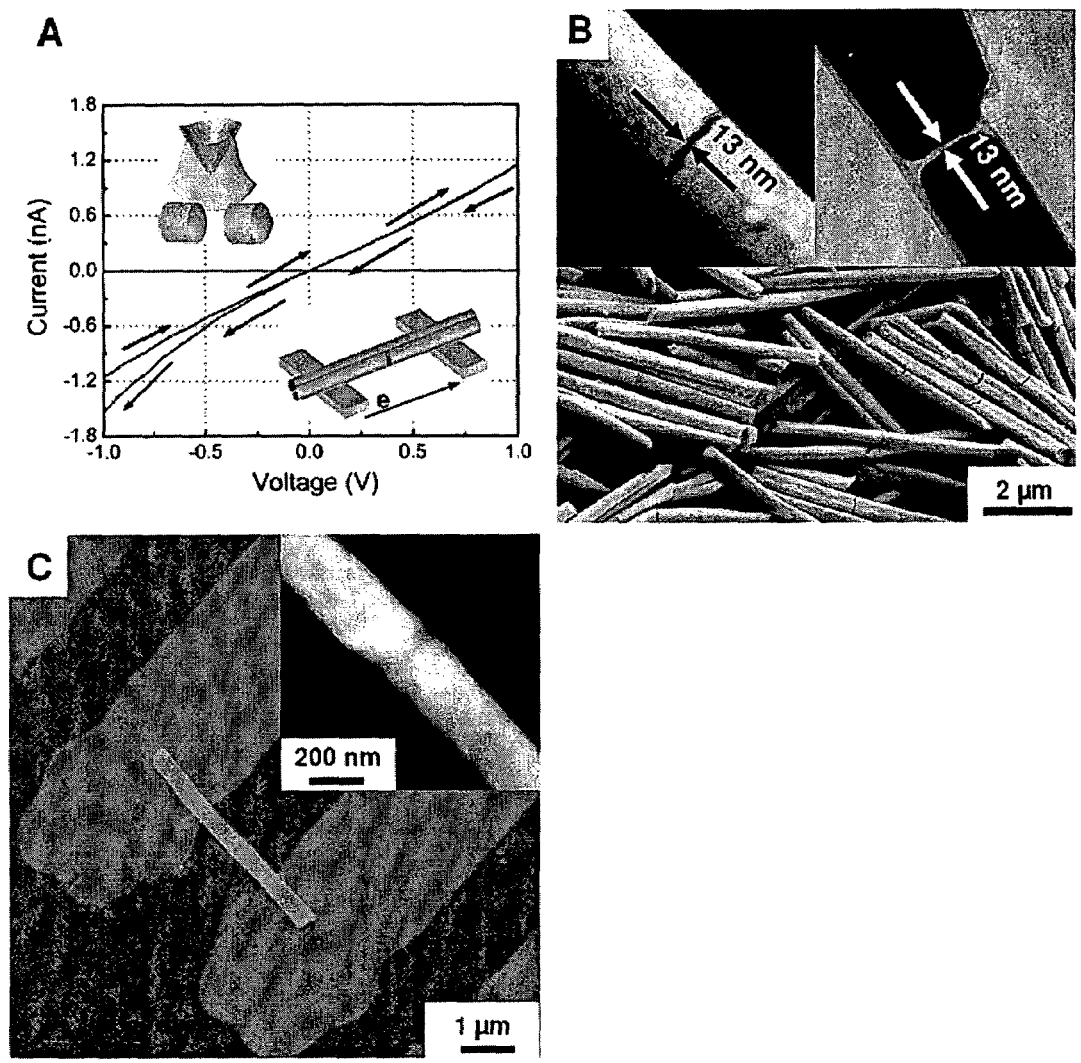
FIG. 8A shows the I-V characteristics of nanowires after silica coating and etching with the inset describing the dippen lithography (DPN) process.
FIG. 8B is a FESEM image of a nanowire created with a 13 nm gap.
FIG. 8C is a FESEM image of a nanowire created with a 13 nm gap, immobilized on microelectrodes and further modified using DPN to deposit a mixture of polyethylene oxide and self-doped Ppy.

A significant issue involving the characterization and utility of gaps fabricated by OWL pertains to their transport properties. For nanowires having a silica bridging substrate, the micrometer scale metal ends can be used as electrically isolated electrode leads that can be interfaced with larger microelectrode electronic circuitry. Nanowires of this type have been characterized by current versus voltage measurements and exhibit insulating behavior (FIG. 8A, horizontal trace). Therefore, the nanowires of the present invention are contemplated for use in microelectrode applications.

The gaps within the nanowires can be functionalized with many materials in a site-specific manner using, for example, DPN (Piner et al, *Science*, 283, 661, 1999 and Ginger et al, *Angew. Chem. Int. Ed.*, 43, 30, 2004). By using DPN, one can monitor the device architecture in the active region, measure the topography of the nanowires, and, simultaneously, functionalize the nanowire gaps with molecule-based materials. Therefore, modified nanowires produced using OWL are contemplated. Modification at site-specific points using DPN is particularly contemplated, as is deposition of conducting polymers using DPN.

The present novel lithographic process allows one to generate designed gap structures on nanowire templates. The process is remarkably controllable, high yielding, easy to implement, does not require sophisticated and expensive instrumentation and facilities, and allows manipulation of an important class of structures that are not easily manipulated with conventional lithographic tools. The ability to make gap or notched structures with nanowires via OWL and relatively inexpensive instrumentation will facilitate the study of the electronic properties of nanomaterials and open avenues to the preparation of novel disk array structures, which could be designed to have unusual optical properties as a function of gap and metal segment size (e.g., plasmon waveguides as disclosed in Maier et al, *Nature Mater.*, 2, 229, 2003 or in surface enhanced raman scattering as disclosed in Kniepp et al, *Chem. Rev.*, 99, 2957, 1999). The present nanowires also can be assembled into arrays of disks and/or rods, depending on the length of the segment compared to its diameter. In accordance with an important feature of the present invention, all the remaining segments, either as arrays of rods or disks, are aligned linearly, which has not been achieved consistently in the field of nanoassemblies prior to this disclosure.

Therefore, a further aspect of this invention is to provide plasmon wires. Plasmon wires are nanodisk structures of nanowires, wherein the gaps or notches of the nanowires are aligned and the metal segments of the nanowires are aligned. This alignment of the gaps in the nanowires allows for the plasmon wires to propagate light through coupled plasmons. Such light propagation is discussed in detail in Schuck et al., *Phys Rev Lett*, 94, 017402, 2005; Maier et al., *Phys Rev B*, 65, 193408, 2002; and Rechberger et al., *Optics Comm*, 220, 137, 2003. Also called photonic crystals, these plasmon wires are important developments in new electronic and optical devices.

Plasmon wires are structures that restrict the propagation of particular wavelengths of electromagnetic radiation by the use of destructive interference and can be designed for very complex routing of light and other such electromagnetic radiation. Furthermore, the gaps between segments of a plasmon wire can act as resonant cavities. The high electromagnetic field strengths that can be generated by the excitation of such cavities can induce novel and useful non-linear effects in materials contained within these gaps. Both the diffractive and resonant forms of such plasmon wire devices find utility in lasers, filters, communications, sensors, and similar applications.

A plasmon wire may be used for a specific application which requires design control of the bandgap; those wavelengths that are "forbidden" (do not pass through the structure) and/or the narrow band of transmitted wavelengths within the "forbidden" range of wavelengths.

Plasmon wires comprising nanowires of the present invention are one dimensional periodic structures. The periodicity of the gaps or notches produced via OWL allow for tailoring of desired end properties of the plasmon wire, such as suppression or enhancement of various wavelengths of interest.

EXAMPLES

Synthesis of Multicomponent Metal-Conducting Polymer-Metal Nanorods

In a typical experiment, a thin layer of silver (200 nm) was evaporated on one side of an alumina filter (Whatman International Ltd, d=13 mm, pore size—20 nm; the pore diameter in the central region of the filter is substantially larger than the quoted 20 nm) and served as a cathode in a three electrode electrochemical cell after making physical contact with aluminum foil. Platinum wire was used as a counter electrode, and silver/silver chloride (Ag/AgCl) was used as the reference electrode. The nanopores were filled by the electrochemical deposition of Ag (Technic ACR silver RTU solution from Technic, Inc.) at a constant potential, −0.9 V vs. Ag/AgCl, by passing 1.5 C/cm$^2$ for 30 minutes. An Au segment then was electroplated from Orotemp 24 RTU solution (Technic, Inc.) at −0.9 volts (V) vs. Ag/AgCl followed by a conducting polymer segment from various plating solutions at positive potentials. For Ppy segments, the solution was a mixture of 0.5 M pyrrole and 0.2 M tetraethylammonium tetrafluoroborate in acetonitrile, and the applied potential was 1.0 V vs. Ag/AgCl. For polyaniline segments, an aqueous solution containing 0.5 M aniline and 0.2 M perchloric acid was used for polymerization. The polymerization potential was 1.0 V vs. Ag/AgCl. The Cd segment was deposited from an aqueous solution of 0.3 M cadmium sulfate and 0.25 M sulfuric acid at −0.8 V vs. Ag/AgCl.

The procedure involving Au was repeated to form the final capping segment. Each segment length was controlled by monitoring the charge passed through the membrane. The first 2.6 μm (±0.2) long segment of Au was generated by passing 2.3 coulombs. The 1 μm (±0.4) segment of Ppy required 0.1 C, and the final 2.4 μm (±0.2) Au segment required 2.3 C (the exposed membrane surface area is about 1 cm$^2$). The Ag backing and alumina membrane were dissolved with concentrated nitric acid and 3M sodium hydroxide solutions, respectively. The rods were rinsed repeatedly with distilled water until the pH of the solution was 7.

Preparation of Microelectrodes and Electrical Transport Measurements of Single Nanorod Devices Electrodes were fabricated via two separate steps. First, contact pads of thermally evaporated layers of 45 nm Au and 5 nm chromium (Cr) were patterned using photolithography onto a silicon (Si) wafer with a 5000 Å thermally grown oxide. Next, electron beam lithography (EBL) was utilized to define an inner electrode pattern (25 nm-thick Au on 7 nm-thick Cr) that was connected to contact pads. EBL was performed using a Hitachi S4500 SEM equipped with a Nabity Pattern Generation System (NPGS, JC Nabity Lithography Systems, Bozeman, Mont.) at 30 kV acceleration voltage and 15 pA beam current. One drop of the aqueous solution of nanorods was deposited on a chip with prefabricated electrodes and the chip was dried in vacuum. After identifying an area where only a single nanorod bridged the prefabricated electrodes, the underlying electrodes were wire-bonded to a chip carrier using a wedge wirebonder (K&S 4526 wirebonder, Kulick & Soffa, Willow Grove, Pa.). The current-voltage (I-V) characteristics of a majority of the devices were obtained using a shielded, temperature controlled cryostat (OptistatCF—continuous flow, exchange gas cryostat, Oxford Instruments, England) equipped with coaxial connections. All the measurements were made in the absence of light. For all measurements, a 16-bit digital acquisition board (DAQ, National Instruments, DL Instrument, Ithaca, N.Y.) and the output voltage of the preamplifier was measured using either an analog-to-digital input on the 16-bit DAQ board, or with an electrometer (Model 6430, Keithley Electronics, Cleveland, Ohio).

Analysis of Multicomponent Nanorods

An Au-Ppy-Au nanorod produced via the above-disclosed procedure was observed using Field Emission Scanning Electron Microscopy (FESEM). Optical microscopy images show a dark Ppy domain sandwiched between two bright segments of Au (see FIG. 1A). Single nanorod devices were prepared from these Au-Ppy-Au nanorods at different temperatures by depositing multicomponent Au-Ppy-Au nanorods on top of a microelectrode array, These nanorod devices were assessed for their electronic properties (see FIG. 2A inset).

Analysis of the I-V curves and the corresponding electrical conductivities of the Au-Ppy-Au nanorods provides two important observations. First, the room temperature conductivity of the polymer segment (about 3 mS/cm) is six orders of magnitude lower than the metallic segments, and all data are consistent with Ohmic contact between the Ppy and Au junctions. Indeed, the inner polymer segments dictate the electric properties of the hybrid three-component system, and the two Au segments function simply as electrical leads to the microscopic circuitry. Second, the I-V response for the Au-Ppy-Au nanorod becomes slightly nonlinear as the temperature decreases (see FIG. 2B). Such nanorods exhibit an Arrhenius-type temperature dependence with respect to conductivity, characteristic of thermally activated charge transport within the segment of Ppy (see FIG. 2B insert). The semiconducting behavior of the Au-Ppy-Au nanorods is reminiscent of that observed for electrochemically polymerized bulk Ppy films. The experimentally determined activations energy ($E_a$=about 0.07 eV) of the Au-Ppy-Au nanorod is in good agreement with the values reported for a moderately doped bulk Ppy film and a nanotubular thin film structure (see FIG. 2B insert) (Watanabe et al, *Macromolecules*, 22, 4231-4235, 1989; Park et al, *Thin Solid Films*, 438, 118, 2003). Because the polymer segments for these nanostructures were generated by oxidative polymerization, they are p-type.

Preparation and Characterization of Multicomponent Nanorods with a Semiconductor Segment.

Gold-polypyrrole-cadmium-gold nanorods can be prepared via the above-disclosed process. The chemical composition of each inorganic segment was confirmed by energy dispersive X-ray spectroscopy (EDX) elemental mapping experiments (see FIGS. 3A-3D). The FESEM of an individual rod clearly shows two interfaces (from left to right) between the Ppy and Cd segments, and between the Cd and Au segments, see FIG. 3C. The EDX analysis of the dotted region in FIG. 3C exhibits characteristic elemental signatures for Cd and Au, see FIG. 3D. All data are consistent with the asymmetric junction structure within the single nanorod.

Figure 3:
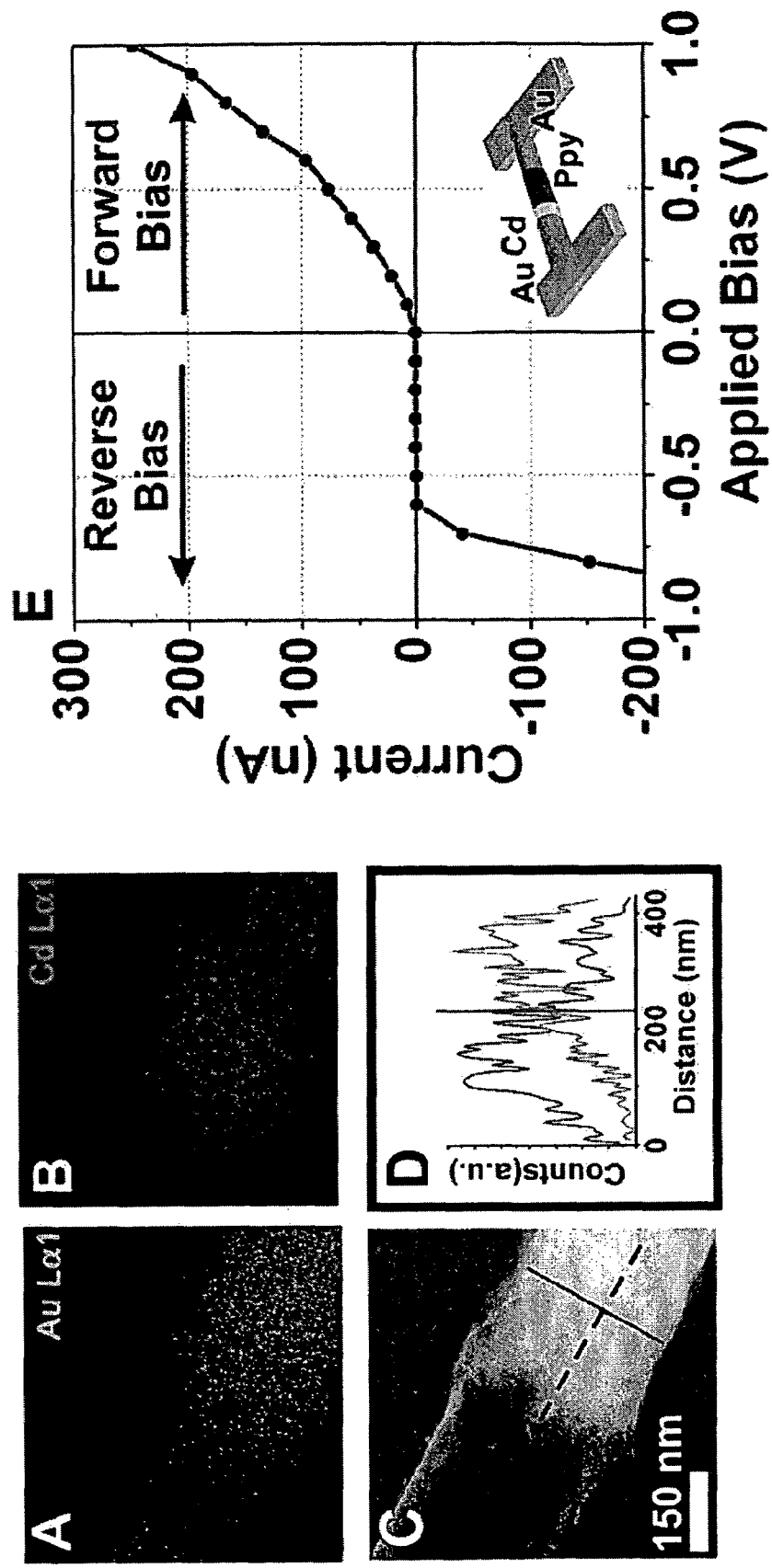
FIG. 3A is an energy dispersive X-ray (EDX) spectroscopy mapping for the Au segment in a single Au-Ppy-Cd—Au nanorod.
FIG. 3B is an EDX spectroscopy mapping for the Cd segment in a single Au-Ppy-Cd—Au nanorod.
FIG. 3C is a FESEM image of the Au-Ppy-Cd—Au nanorod.
FIG. 3D is a graph of the X-ray profile for the Cd (dark trace) and Au (pale trace) segments over the dashed trace shown in the image in FIG. 3C.
FIG. 3E is the I-V characteristics for a single Au-Ppy-Cd—Au nanorod at room temperature.

Current vs. voltage measurements on devices constructed from single Au-Ppy-Cd—Au rods exhibit "diode" behavior at room temperature, see FIG. 3E. The typical response is asymmetric and non-Ohmic. In the forward bias, there is a positive voltage on the Au segment interfaced with the Cd segment. Therefore, holes move from the Ppy segment to the Cd segment during the forward bias. In reverse bias, current does not flow until the bias overcomes the breakdown potential (−0.61 V). The turn-on voltage for these diode nanorods is about 0.15 V, almost 1 V lower than rods prepared to date via the layer-by-layer assembly method (Kovtyukhova et al, *J Phys Chem B*, 105, 8762, 2001). The rectifying ratio (i.e., forward bias current/reverse bias current) is 200 at ±0.6 V. The I-V characteristics of the Au-Ppy-Cd—Au nanorods at room temperature suggest that a Schottky-like junction is formed at the Ppy/Cd interface due to the difference in work function for the two materials (Abthagir et al, *J Appl Polym Sci*, 81, 2127, 2001; Watanabe et al, *Macromolecules*, 22, 4231, 1989; Sze, *Physics of Semiconductor Devices*, $2^{nd}$ ed., Wiley: New York, 1981). The difference in work function ($\Delta\Phi$) between a metal such as Cd and a moderately doped p-type semiconducting Ppy is about 0.68 eV, which is larger than that for Au and Ppy ($\Delta\Phi$(Au-Ppy) about 0.1 eV) based upon the assumption that the work function of an electrochemically polymerized Ppy film with a similar doping level is about 4.9 to about 5.1 eV as reported in Abthagir et al, *JAppl Polym Sci*, 81, 2127, 2001 and Watanabe et al, *Macromolecules*, 22, 4231, 1989. By fitting the experimental I-V responses to the model for metal semiconductor Schottky junctions (Abthagir et al, *J Appl Polym Sci*, 81, 2127, 2001; Sze, *Physics of Semiconductor Devices*, $2^{nd}$ ed., Wiley: New York, 1981), a barrier height ($\Phi_{BH}$) for the Ppy/Cd junction was determined to be about 0.68 eV, and is in good agreement with the reported values of electrochemically polymerized bulk Ppy/indium junctions (Watanabe et al, *Macromolecules*, 22, 4231, 1989).

On-Wire Lithography Process

Figure 9:
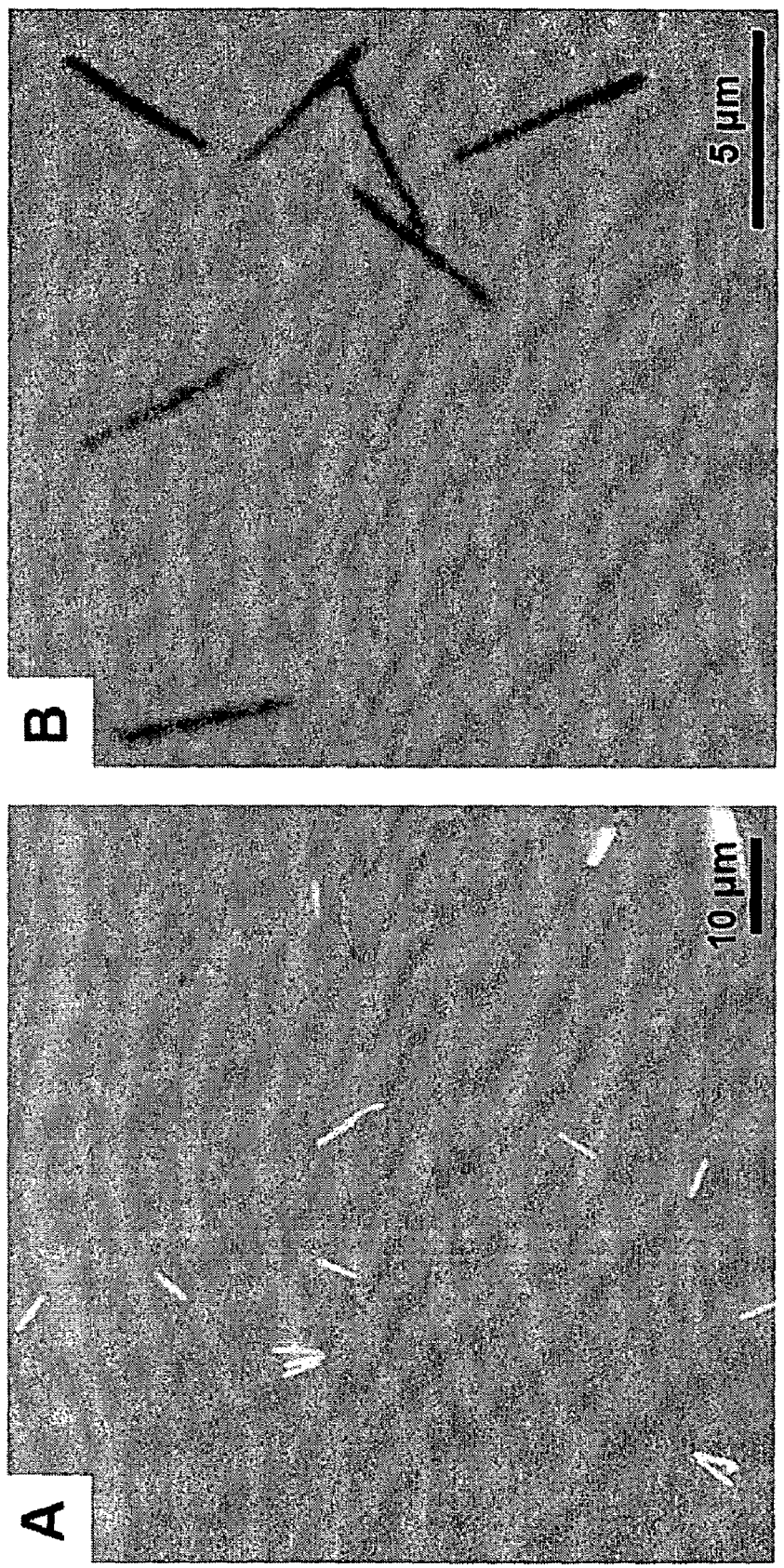
FIG. 9A is a bright-field optical image of metallic nanowires dispersed on a glass slide.
FIG. 9B is a bright-field optical image of wire-shaped pits after the wires are released.

The materials can be electrochemically deposited in porous alumina templates in a controlled fashion from suitable plating solutions via well-established methods (see FIG. 6) (Martin, *Science*, 266, 1961, 1994; Routkevitch, et al, *J. Phys. Chem.*, 100, 14037, 1996; Nicewarner-Pena et al, *Science*, 294, 137, 2001; Kowtyukhova et al, *Chem. Eur. J*, 8, 4354, 2002). The length of each segment is tailored by controlling the charge passed during the electrodeposition process (see FIG. 10). The resulting multi-metallic wires then are released from the template by dissolution of the template via known procedures (Park et al, *Science*, 303, 348, 2004). In one example, an aqueous suspension of Au—Ni nanorods is cast upon a glass microscope slide pre-treated with a piranha solution which makes the slide hydrophilic. After drying, a layer of silicon dioxide was deposited on the nanorods, using plasma enhanced chemical vapor deposition (PECVD) (see FIG. 9A). This results in one side of the nanorod being coated with silicon dioxide while the other side, which is protected by the microscope slide substrate, remains uncoated. Sonication of the substrate leads to the release of the coated nanorods into solution (FIG. 9B). The final step of the OWL process involves the selective wet-chemical etching of the sacrificial segments. Nickel segments can be removed from the rods by treating the rods with concentrated nitric acid for 1 hr. This results in the generation of nanowire structures with gaps precisely controlled by the length of the original Ni segments (FIG. 6). The Au segments remaining after removal of the Ni segments are held in place by the stripe of silicon dioxide. As silicon dioxide is an insulator, the Au segments can be electrically connected to one another if the nanowires are coated with Au/Ti rather than silicon dioxide in this process. In another alternative, the nanorods are comprised of Au and Ag segments, the sacrificial Ag segments are removed by treating the coated nanorods with an etching solution containing methanol, 30% ammonium hydroxide, and 30% hydrogen peroxide (4:1:1 v/v/v) for 1 hour. Numerous other combinations of materials and etchants can likewise be used for such purposes depending upon the intended use of the structures formed.

Figure 7:
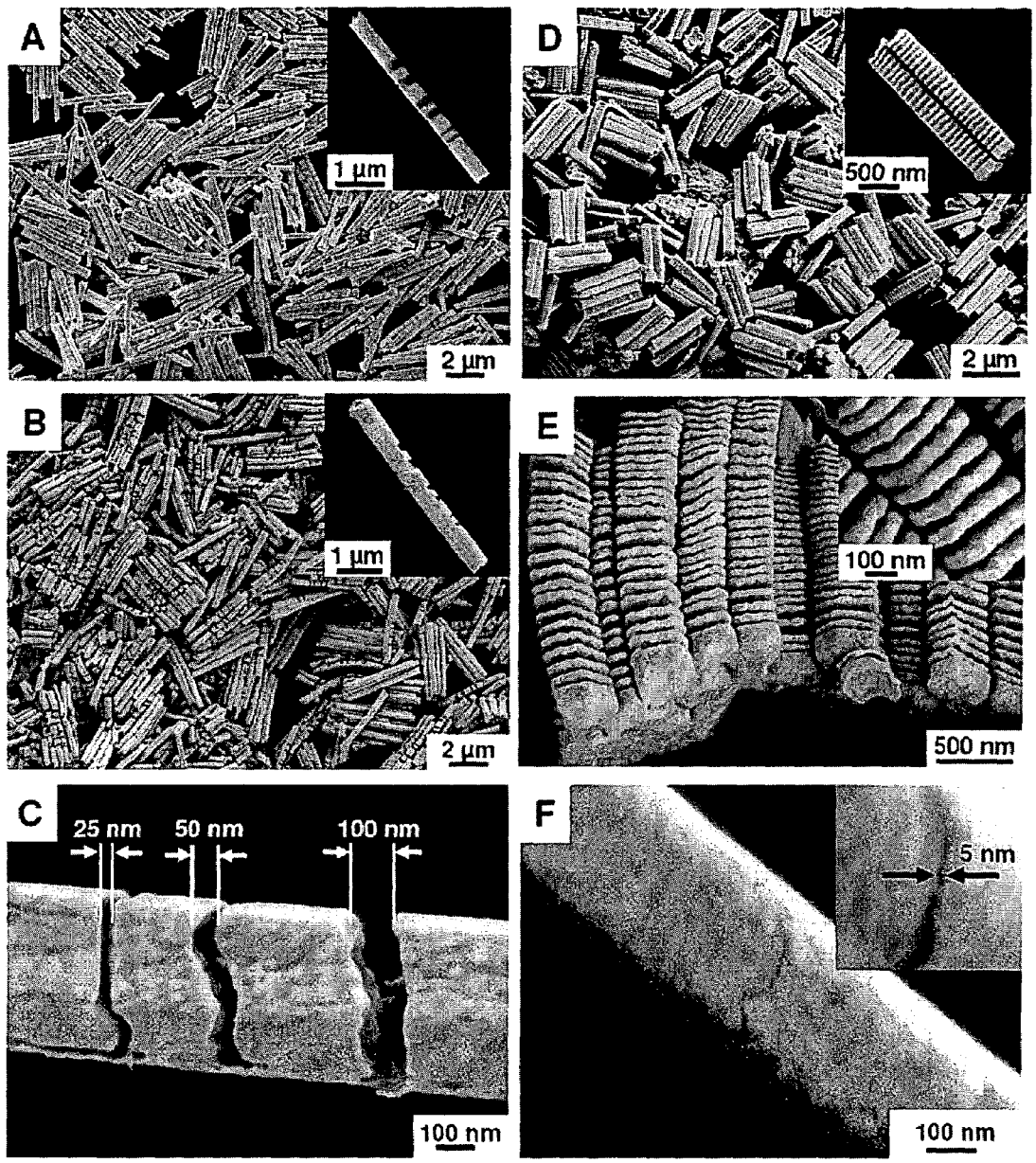
FIG. 7A is the FESEM image of a nanorod having Au and Ag segments.
FIG. 7B is the FESEM image of a nanorod having Au and Ag segments after etching.
FIG. 7C is the FESEM image of a nanowire having a 25 nm gap, a 50 nm gap and a 100 nm gap.
FIG. 7D is a FESEM image of a nanorod structured assembly having nickel (Ni) and Au segments.
FIG. 7E is a FESEM image of a nanowire structured assembly having Ni and Au segments after coating with silica and subsequent removal of the Ni segments.
FIG. 7F is a FESEM image of a 5 nm nanogap achieved using OWL.
Figure 11:
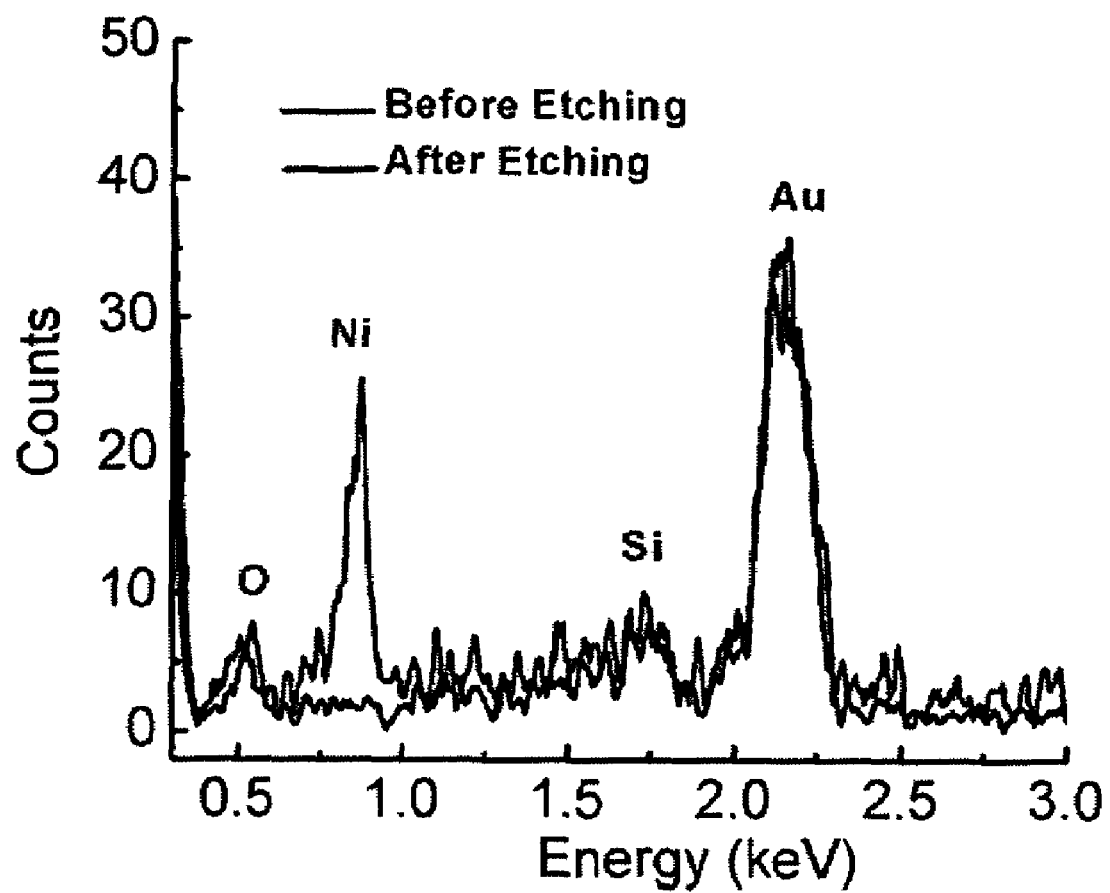
FIG. 11 shows the EDX spectra of nanogap wires before and after etching of Ni.

The physical dimensions and segment compositions of the nanowires, before and after etching, were determined by FESEM and EDX (see FIG. 7A-7F and FIG. 11). Structures made of Ag and Au before coating with Au/Ti and wet-chemical etching exhibit a bright contrast for the Au regions and a dark contrast for the Ag regions (FIG. 7A). After etching, the notched structures are clearly visible (FIG. 7B). The EDX spectra before etching shows Ni present, and after etching the Ni peak has disappeared. The Si and oxygen peaks correspond to the presence of the silica coating (FIG. 11). The average length of the wires is 4.5±0.25 µm, and each wire exhibits two 210±10 nm, two 140±8 nm, and two 70±5 nm notches (FIG. 7B). The diameter of each wire is 360±20 nm. Certain views show the Au/Ti backing, which bridges the notched regions on these structures (FIG. 7B, inset). Structures with sub-100 nm gap sizes can routinely be generated via OWL. To demonstrate this capability, OWL was used to prepare wires having 25, 50, and 100 nm gaps (FIG. 7C).

Multi-segment nanorods composed of Ni and Au segments were synthesized using electrochemical deposition into a porous alumina membrane. A thin layer of Ag (200 nm) was evaporated on one side of an alumina filter (Whatman International Ltd, d=13 mm, pore size=20 nm; the pore diameter in the central region of the filter is substantially larger than the quoted 20 nm) and served as a cathode in a three electrode chemical cell after making physical contact with aluminum foil. Platinum wire was used as a counter electrode, and Ag/AgCl was used as the reference electrode. The nanopores were partially filled with Ag, leaving headroom to accommodate the growth of additional domains (Technic ACR silver RTU solution from Technic, Inc.) at a constant potential, −0.9 V vs. Ag/AgCl, by passing 1.5 C/cm$^2$ for 30 min. An Au segment then was electroplated from Orotemp 24 RTU solution (Technic, Inc.) at −0.9 V vs. Ag/AgCl followed by a Ni segment from nickel sulfamate RTU solution (Technic, Inc.) at −0.9 V vs. Ag/AgCl. The procedure involving Au was repeated to form a second Au segment. Each segment length was controlled by monitoring the charge passed through the membrane. The first 1.4 µm (±0.2) long segment of Au was generated by passing 1.3 C. The Ag backing and the alumina membrane then were dissolved with concentrated nitric acid and 3 M sodium hydroxide solutions, respectively. The rods were repeatedly rinsed with nanopure water until the solution reached at pH of 7. Nanorods containing more than three segments are prepared by repeating the above steps until the desired number of segments have been constructed. These added segments may be constructed of the same or different materials than used in the construction of the initial three segments, by appropriate selection of the plating materials and conditions in the manner known to those of skill in the art.

To demonstrate the capabilities of OWL in the preparation of repeating nanostructures having regular 40 nm gaps, nanowire structures with twenty-two 40 nm Ni segments and twenty-three 40 nm Au segments were made (FIG. 7D). Silicon dioxide was used as the bridging material. After etching, the removal of the Ni segments was confirmed by EDX spectroscopy of the nanowires (FIG. 11). The Ni peak is present before etching, and is absent after. The Si and oxygen peaks in the after etching spectrum are due to the presence of silica as the coating material. Face-to-face disk arrays with 40 nm gaps were generated (FIG. 7E). The statistical variation of gap size generally increases with decreasing gap size, but is typically less than 10%. Note that in some images the variation looks greater, but this is due to mechanical stress on the wire structures, which results in a "fanning" effect with respect to the gaps. The smallest gap structures generated via OWL are 5 nm (FIG. 7E), but with appropriate electrochemical control, smaller gaps can be gerneated, such as down to 2 nm and preferably 1 nm.

To test the properties of these structures and their suitability for making transport measurements on small amounts of materials containing within the gaps, a droplet of a suspension containing wires with 13 nm gaps was evaporated on a microelectrode array fabricated by: conventional photolithography (FIGS. 8B and 8C). The electrodes were 3 μm wide and separated by 2 μm. Some of the wires end up bridging the microelectrodes, allowing for easy electrical measurements of the structures.

Further Modified Nanowires with Photosensitivity

Figure 12:
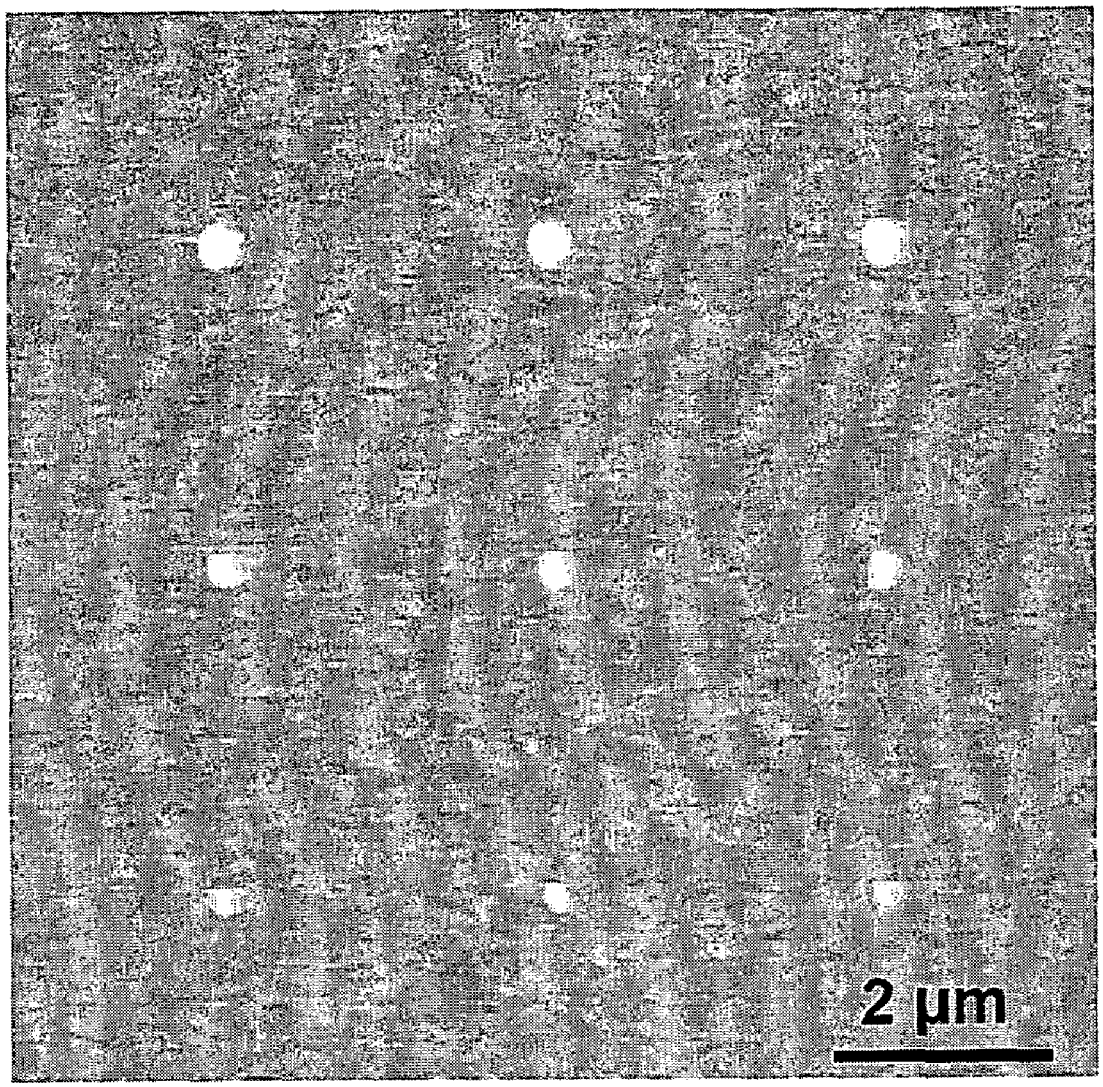
FIG. 12 is an atomic force microscopy (AFM) topography image of dot patterns composed of 1:1 (w/w) mixture of polyethylene oxide:Ppy, generated by DPN.

A mixture of 1:1 (w/w) polyethylene oxide (PEO) and Ppy was deposited into the gaps of a nanowire using DPN. The mixture consisted of 3 mL of PEO (0.05 g, $M_v \approx 100,000$, Aldrich) in acetonitrile and 1 mL of 5% aqueous self-doped Ppy (Aldrich). Contact times between tip and substrate were 2, 1, and 0.5 sec for the large, medium and small sized dots, respectively (FIG. 12, top to bottom). The chamber humidity was 80% and the tip substrate contact force was 1.0 nN. The DPN patterning was done with a ThermoMicroscopes CP AFM interfaced with customized software. Nanoink, type S-1, AFM probes having a spring constant of 0.041 N/m were used for these depositios.

A SEM image of nanowires having polymer deposited in the gaps of the nanowire shows the clear contrast between the clean Au surface and the polymer covered area including the gap (FIG. 8C, inset). Current vs. voltage measurements after deposition of the polymer shows a linear response from −1.0 V to +1.0 V, characteristic of a conducting polymer (FIG. 8A). The measured conductance of 1.1 nS is similar to the value of 9.6 nS determined by functionalizing 60 nm conventional nanoelectrode gaps fabricated by EBL. There is no noticeable I-V hysteresis between the forward (from −1.0 V to +1.0 V) and backward (from +1.0 V to −1.0 V) scans, and they are highly linear at room temperature, as expected for a structure with an Ohmic-like contact in a symmetric device configuration. To prove that the response is indeed due to the polymer within the gap, the I-V response as a photoexcitation was studied using a Xe lamp (150 W). The I-V response for the polymer filled nanowire becomes slightly more conductive upon Xe light exposure. During the backward scan, the device was irradiated with the Xe lamp starting at −0.1 V (FIG. 8A, grey arrows), and a change in slope in the current voltage response was observed. The transient conductance change between 1.1 nS in the dark to 1.6 nS when irradiated is consistent with an increase in charge carrier density expected if the gap was filled with the p-type Ppy.

What is claimed is:

1. A lithographic process for producing a nanowire comprising the steps of:
    a) providing a nanorod comprising alternating segments of a metal and a sacrificial metal;
    b) depositing a coating onto one side of the nanorod; and
    c) subjecting the coated nanorod to etching to remove the sacrificial metal segments from the nanorod and thereby produce a nanowire having gaps at positions previously occupied by the sacrificial metal.

2. The lithographic method of claim 1 further comprising a step of filling the gaps with a filler.

3. The lithographic method of claim 2 wherein the filler is deposited using dip-pen lithography.

4. The lithographic method of claim 2 wherein the filler is a conducting polymer.

5. The lithographic process of claim 1 wherein the metal of the nanorod is gold.

6. The lithographic process of claim 1 wherein the sacrificial metal is nickel or silver.

7. The lithographic process of claim 1 wherein the coating is a gold/titanium alloy or silicon dioxide.

8. The lithographic process of claim 1 wherein the gaps of the nanowire independently have a width of about 2 nm to about 5 μm.

* * * * *